(12) United States Patent
Hancock

(10) Patent No.: US 12,023,094 B2
(45) Date of Patent: Jul. 2, 2024

(54) ELECTROSURGICAL ABLATION INSTRUMENT

(71) Applicant: Creo Medical Limited, Chepstow (GB)

(72) Inventor: Christopher Paul Hancock, Bath (GB)

(73) Assignee: CREO MEDICAL LIMITED, Chepstow (GB)

( * ) Notice: Subject to any disclaimer, the term of this patent is extended or adjusted under 35 U.S.C. 154(b) by 1009 days.

(21) Appl. No.: 16/766,422

(22) PCT Filed: Dec. 20, 2018

(86) PCT No.: PCT/EP2018/086237
§ 371 (c)(1),
(2) Date: May 22, 2020

(87) PCT Pub. No.: WO2019/129648
PCT Pub. Date: Jul. 4, 2019

(65) Prior Publication Data
US 2020/0360085 A1    Nov. 19, 2020

(30) Foreign Application Priority Data

Dec. 27, 2017   (GB) ..................... 1721995

(51) Int. Cl.
*A61B 18/14*   (2006.01)
*A61B 8/12*    (2006.01)
(Continued)

(52) U.S. Cl.
CPC ............ *A61B 18/1815* (2013.01); *A61B 8/12* (2013.01); *A61B 18/1492* (2013.01);
(Continued)

(58) Field of Classification Search
CPC ............ A61B 18/1206; A61B 18/1492; A61B 18/1815; A61B 2017/0034;
(Continued)

(56) References Cited

U.S. PATENT DOCUMENTS 5,707,452 A * 1/1998 Dandl ............... H01J 37/32688
                                                118/723 MR
5,861,021 A   1/1999 Thome et al.
(Continued)

FOREIGN PATENT DOCUMENTS

JP    H09-140723 A    6/1997
WO    WO 2017/174513 A1   10/2017

OTHER PUBLICATIONS

International Search Report and the Written Opinion issued by the International Searching Authority in corresponding International Patent Application No. PCT/ EP2018/086237, dated Apr. 4, 2019.
(Continued)

*Primary Examiner* — Michael F Peffley
*Assistant Examiner* — Amanda L Zink
(74) *Attorney, Agent, or Firm* — ArentFox Schiff LLP

(57) ABSTRACT

An electrosurgical instrument having a microwave ablation antenna dimensioned to be suitable for insertion into a pancreas via a surgical scoping device, to provide a rapid and accurate alternative to known RF ablation techniques. The electrosurgical instrument comprises: a proximal coaxial transmission line for conveying microwave electromagnetic (EM) energy; a distal radiating portion; and an intermediate impedance transformer arranged to match an impedance of the coaxial transmission line to an impedance of the distal radiating portion, wherein the distal radiating portion comprises a microwave antenna for emitting the microwave EM energy conveyed by the coaxial transmission line, wherein the distal radiating portion has a maximum outer diameter less than an outer diameter of the coaxial transmission line. With these features, the instrument is able to deliver microwave energy via a small diameter structure.

17 Claims, 3 Drawing Sheets

(51) Int. Cl.
*A61B 18/12* (2006.01)
*A61B 18/18* (2006.01)
*A61B 17/00* (2006.01)
*A61B 18/00* (2006.01)
*A61B 90/00* (2016.01)

(52) U.S. Cl.
CPC ............... *A61B 2017/0034* (2013.01); *A61B 2018/00482* (2013.01); *A61B 2018/00577* (2013.01); *A61B 2018/00994* (2013.01); *A61B 2018/126* (2013.01); *A61B 2018/1823* (2013.01); *A61B 2018/1853* (2013.01); *A61B 2018/1861* (2013.01); *A61B 2018/1869* (2013.01); *A61B 2090/036* (2016.02); *A61B 2218/002* (2013.01); *A61B 2218/007* (2013.01)

(58) Field of Classification Search
CPC .......... A61B 2018/00482; A61B 2018/00577; A61B 2018/00994; A61B 2018/126; A61B 2018/1823; A61B 2018/1853; A61B 2018/1861; A61B 2018/1869; A61B 2018/1892; A61B 2090/036; A61B 2218/002; A61B 2218/007; A61B 8/12
See application file for complete search history.

(56) References Cited

U.S. PATENT DOCUMENTS

| | | | |
|---|---|---|---|
| 6,325,796 B1 | 12/2001 | Berube et al. | |
| 8,282,632 B2 | 10/2012 | Rossetto | |
| 11,660,137 B2* | 5/2023 | Davies | A61B 18/1482 606/41 |
| 2011/0077632 A1* | 3/2011 | Rossetto | A61B 18/1815 606/33 |
| 2012/0259326 A1 | 10/2012 | Brannan et al. | |
| 2013/0256302 A1* | 10/2013 | Chu | H05B 1/025 219/709 |
| 2014/0025054 A1* | 1/2014 | Surti | A61B 18/1492 606/41 |
| 2014/0046174 A1 | 2/2014 | Ladtkow et al. | |
| 2014/0290830 A1 | 10/2014 | Brannan | |
| 2016/0081743 A1 | 3/2016 | Brannan et al. | |
| 2016/0095657 A1 | 4/2016 | Brannan | |
| 2017/0231695 A1 | 8/2017 | Dickhans et al. | |

OTHER PUBLICATIONS

Search Report Issued by the United Kingdom Patent Office in corresponding United Kingdom Patent Application No. GB1721995.7, dated May 24, 2018.

Written Opinion of the International Preliminary Amendment issued from the International Preliminary Examining Authority in corresponding International Application No. PCT/EP2018/086237, dated Feb. 19, 2020.

Written Opinion of the International Preliminary Amendment issued from the International Preliminary Examining Authority in corresponding International Application No. PCT/EP2018/086237, dated May 12, 2019.

* cited by examiner

ELECTROSURGICAL ABLATION INSTRUMENT

CROSS-REFERENCE TO RELATED APPLICATIONS

This application is a National Stage entry of International Application No. PCT/EP2018/086237, filed on Dec. 20, 2018, which claims priority to British Patent Application No. 1721995.7, filed on Dec. 27, 2017. The disclosures of the priority applications are hereby incorporated in their entirety by reference.

FIELD OF THE INVENTION

The invention relates to an electrosurgical instrument for delivering radiofrequency and microwave energy to biological tissue in order to ablate the target tissue. In particular, the probe is configured to be insertable through a channel of a surgical scoping device or catheter that can be introduced to a treatment site in a non-invasive manner. The probe may be arranged to ablate tissue, such as a tumour, cyst or other lesion. The probe may be particularly suited for treatment in the pancreas.

BACKGROUND TO THE INVENTION

The application of heat energy to biological tissue is well known as an effective method of killing cells. For example, the application of radiofrequency or microwave energy can heat and thus ablate (destroy) biological tissue. This method may in particular be used for the treatment of cancer.

A technique of treating tissue in the pancreas using endoscopic ultrasound guided radiofrequency ablation is known (Pai, M., et al.: *Endoscopic ultrasound guided radiofrequency ablation, for pancreatic cystic neoplasms and neuroendocrine tumors*, World J Gastrointest Surg 2015 Apr. 27; 7(4): 52-59). In this technique a conductive wire having a small diameter (e.g. 0.33 mm) is inserted through the working channel of an ultrasound-enabled endoscope. RF power is applied to the wire in conjunction with an external grounded return pad in contact with the patient's skin to coagulate tissue in the liver and pancreas. To ablate lesions it is necessary to apply power for 90-120 seconds, and, in some cases to remove and reposition the wire.

SUMMARY OF THE INVENTION

At its most general, the invention provides an electrosurgical instrument having a microwave ablation antenna dimensioned to be suitable for insertion into a pancreas via a surgical scoping device, to provide a rapid and accurate alternative to known RF ablation techniques. Although the invention may find particular use in the pancreas, it may also be suitable for use in other awkward treatment sites, such as the lungs, etc.

According to the invention, there is provided an electrosurgical instrument comprising: a proximal portion comprising a coaxial transmission line for conveying microwave electromagnetic (EM) energy; a distal radiating portion; and an intermediate impedance transformer arranged to match an impedance of the coaxial transmission line to an impedance of the distal radiating portion, wherein the distal radiating portion comprises a microwave antenna for emitting the microwave EM energy conveyed by the coaxial transmission line, wherein the distal radiating portion has a maximum outer diameter less than an outer diameter of the coaxial transmission line. With these features, the instrument is able to deliver microwave energy via a small diameter structure.

The coaxial transmission line may comprise an inner conductor separated from a proximal outer conductor by a first dielectric material. The coaxial transmission line may be a conventional coaxial cable. Advantageously, the inner conductor of the coaxial cable may extend beyond a distal end of the proximal outer conductor through the intermediate impedance transformer and into the distal radiating portion. In other words, the intermediate impedance transformer and the distal radiating portion may shall a common coaxial cable. This may be achieved by stripping away the outer conductor of the coaxial transmission line along the a distal portion thereof where the intermediate impedance transformer and the distal radiating portion are to be formed. As discussed below, the first dielectric material may also be used in the intermediate impedance transformer and the distal radiating portion. For example, the first dielectric can be selectively removed in these regions to reduce its diameter. In some cases it may be removed altogether and replaced with other dielectric materials. Alternatively it may be used alone or in combination with other materials.

The proximal outer conductor (i.e. the outer conductor of the coaxial transmission line) may have an outer diameter equal to or less than 3 mm, preferably equal to or less than 2.2 mm. The maximum outer diameter of the distal radiating portion may be equal to or less than 1 mm. The intermediate impedance transformer may have a maximum outer diameter in between that of the proximal outer conductor and the distal radiating portion.

The intermediate impedance transformer is a quarter wavelength coaxial transmission line. Here "quarter wavelength" refers to the wavelength of the microwave energy delivered by the coaxial transmission line. The instrument may be designed for use at a particular frequency of microwave energy, so this length is derivable for any given instrument.

In the quarter wavelength coaxial transmission line, the inner conductor may be separated from an intermediate outer conductor by a second dielectric material having a smaller outer diameter than an outer diameter of the first dielectric material. In one example, the second dielectric material is a reduced diameter portion of the first dielectric material that extends beyond the distal end of the proximal outer conductor. Alternatively or additionally (in that the intermediate impedance transformer may comprise a combination of dielectric materials), the second dielectric material may include or consist of a material having a higher relative permittivity than the first dielectric material.

The inner conductor may extend through the distal radiating portion to form a conductive portion of the microwave antenna. In this example, the inner conductor of the coaxial transmission line therefore extends along the entire length of the instrument.

In another example, a distal conductive finger may be mounted on a distal end of the inner conductor. The distal conductive finger may form a conductive portion of the microwave antenna. In this example, the inner conductor acts as a feed for the microwave antenna. The distal radiating portion may comprise a coaxial feed portion having the microwave antenna formed at a distal end thereof.

The microwave antenna may be a loaded monopole antenna having a distal dielectric material mounted over the conductive portion of the microwave antenna. The distal dielectric material may be a reduced diameter portion of the first dielectric material that extends beyond the distal end of the proximal outer conductor. In this example, the first dielectric material may extend along the entire length of the instrument. Alternatively or additionally, the distal dielectric material may comprise a rigid material having a higher relative permittivity than the first dielectric material. Ceramic or polyether ether ketone (PEEK) may be used. The coaxial feed portion of the distal radiating portion may use the same or a different dielectric material from that which loads the microwave antenna.

A distal end of the microwave antenna may be sharpened to facilitate insertion into tissue. Herein "sharpened" may mean that the distal tip of the instrument tapers to a point, e.g. in a needle-like manner. The sharpened portion may comprise the dielectric material that loads the microwave antenna, or may comprise a protruding portion of the distal conductive finger in the case of an unloaded antenna.

In another example, the microwave antenna may be a slotted antenna. For example, the distal radiating portion may comprise a distal coaxial transmission line having a distal inner conductor separated from a distal outer conductor by a distal dielectric material. The slotted antenna may be formed by removing portions of the distal outer conductor. The removed portions may resemble windows in the distal outer conductor through which the distal dielectric material is exposed. There may be one or more windows along the length of the microwave antenna. Each window may extend around the whole circumference of the distal radiating portion. The windows may be separated by a half wavelength of the microwave energy emitted by the antenna.

The distal inner conductor may be electrically connected to the distal outer conductor at a distal tip of the microwave antenna. This may elongate the shape of the field emitted by the antenna.

Also disclosed herein is an electrosurgical apparatus comprising: a surgical scoping device having an instrument cord configured to be insertable into a patient's body, wherein the instrument cord has an instrument channel formed therethrough; and an electrosurgical instrument according to any preceding claim dimensioned to be insertable through the instrument channel.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less. In embodiments of the invention, the surgical scoping device may be an ultrasound-enabled endoscope.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. The device may delivery energy at more than one of these microwave frequencies. In contrast, this specification uses "radiofrequency" or "RF" to indicate a frequency range that is at least three orders of magnitude lower, e.g. up to 300 MHz, preferably 10 kHz to 1 MHz.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
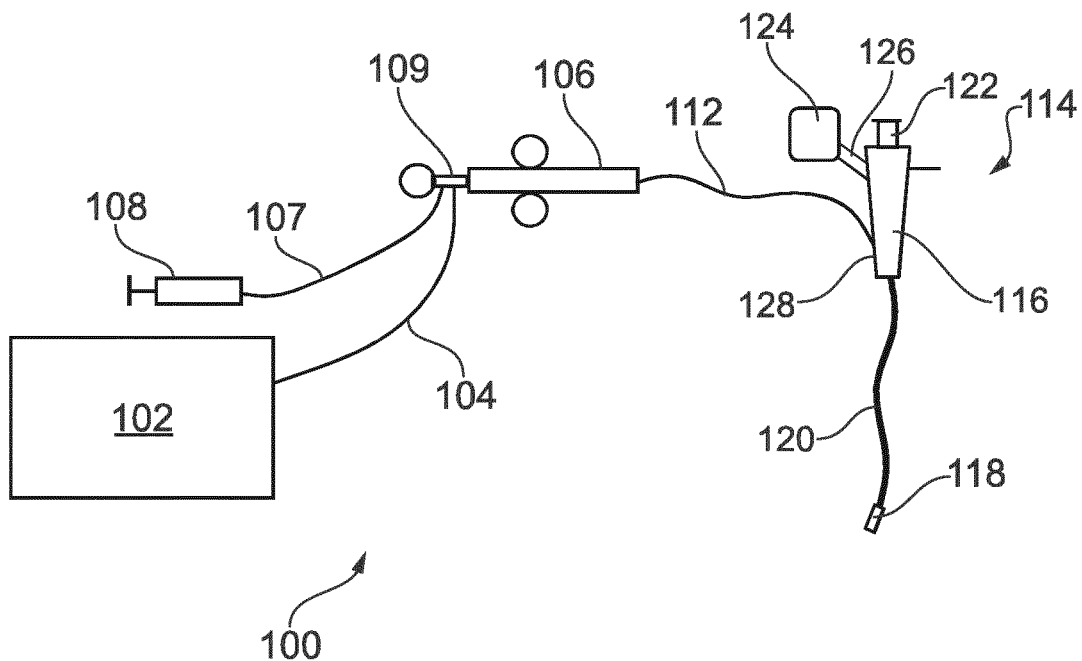
FIG. 1 is a schematic diagram showing an electrosurgical ablation apparatus that is an embodiment of the invention.

FIG. 1 is a schematic diagram of an electrosurgical ablation apparatus 100 that is capable of supplying microwave energy and fluid, e.g. cooling fluid, to the distal end of an invasive electrosurgical instrument. The system 100 comprises a generator 102 for controllably supplying radiofrequency (RF) and microwave energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level.

The generator 102 is connected to an interface joint 106 by an interface cable 104. The interface joint 106 is also connected via a fluid flow line 107 to a fluid delivery device 108, such as a syringe. In some examples, the apparatus may be arranged, additionally or alternatively, to aspirate fluid from the treatment site. In this scenario, the fluid flow line 107 may convey fluid away from the interface joint 106 to a suitable collector (not shown). The aspiration mechanism may be connected at a proximal end of the fluid flow line 107.

If needed, the interface joint 106 can house an instrument control mechanism that is operable by sliding a trigger, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a surgical scoping device 114, which in embodiment of the present invention may comprise an endoscopic ultrasound device.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end or to gather images from the distal end. The body 116 may include a eye piece 122 for viewing the distal end.

An endoscopic ultrasound device typically provide an ultrasound transducer on a distal tip of the instrument cord, beyond an exit aperture of the instrument channel. Signals from the ultrasound transducer may be conveyed by a suitable cable 126 back along the instrument cord to a processor 124, which can generate images in a known manner. The instrument channel may be shaped within the instrument cord to direct an instrument exiting the instrument channel through the field of view of the ultrasound system, to provide information about the location of the instrument at the target site.

The flexible shaft 112 has a distal assembly 118 (not drawn to scale in FIG. 1) that is shaped to pass through the instrument channel of the surgical scoping device 114 and protrude (e.g. inside the patient) at the distal end of the instrument cord.

The structure of the distal assembly 118 discussed below may be particularly designed for use with an endoscopic ultrasound (EUS) device, whereby the maximum outer diameter of the distal end assembly 118 is equal to or less than 2.0 mm, e.g. less than 1.9 mm (and more preferably less than 1.5 mm) and the length of the flexible shaft can be equal to or greater than 1.2 m.

The body 116 includes a power input port 128 for connecting to the flexible shaft 112. As explained below, a proximal portion of the flexible shaft may comprise a conventional coaxial cable capable of conveying the radiofrequency and microwave energy from the generator 102 to the distal assembly 118. Coaxial cables that are physically capable of fitting down the instrument channel of an EUS device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

As discussed above, it is desirable to be able to control the position of at least the distal end of the instrument cord 120. The body 116 may include a control actuator that is mechanically coupled to the distal end of the instrument cord 120 by one or more control wires (not shown), which extend through the instrument cord 120. The control wires may travel within the instrument channel or within their own dedicated channels. The control actuator may be a lever or rotatable knob, or any other known catheter manipulation device. The manipulation of the instrument cord 120 may be software-assisted, e.g. using a virtual three-dimensional map assembled from computer tomography (CT) images.

Figure 2:
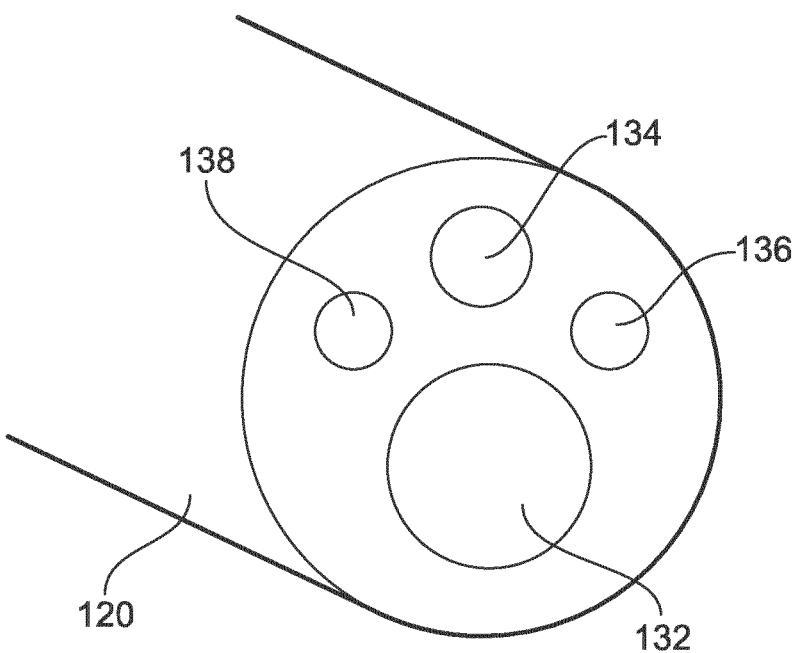
FIG. 2 is a schematic sectional view through an instrument cord of an endoscope that can be used with the present invention.

FIG. 2 is a view down the axis of the instrument cord 120. In this embodiment there are four lumens within the instrument cord 120. The largest lumen is the instrument channel 132. The other lumens comprise an ultrasound signal channel 134 and an illumination channel 136, and a camera channel 138 but the invention is not limited to this configuration. For example, there may be other lumens, e.g. for control wires or fluid delivery or suction.

In one embodiment, the invention may provide an instrument that can perform tissue ablation at the distal end of an EUS system catheter. In order for side effects to be reduced and the efficiency of the instrument to be maximised, the transmitting antenna should be located as close to the target tissue as possible. Ideally, the radiating part of the instrument is located inside (e.g. at the centre of) the tumour during treatment.

The invention may be particularly suited for treatment of the pancreas. In order to reach the target site, the instrument will need to be guided through the mouth, stomach and duodenum. The instrument is arranged to access the pancreas by passing through the wall of the duodenum. This procedure places significant restrictions on the size of the instrument that may pass into the pancreas. Conventionally, instruments having an outer diameter no larger than 1 mm (e.g. 19 gauge) have been used.

The description below presents a number of antenna configurations that are suitable for use in the distal assembly 118 described.

In the following description, unless stated otherwise, the length of a component refers to its dimension in the direction parallel to the longitudinal axis of the coaxial cable/instrument cord.

Figure 3:
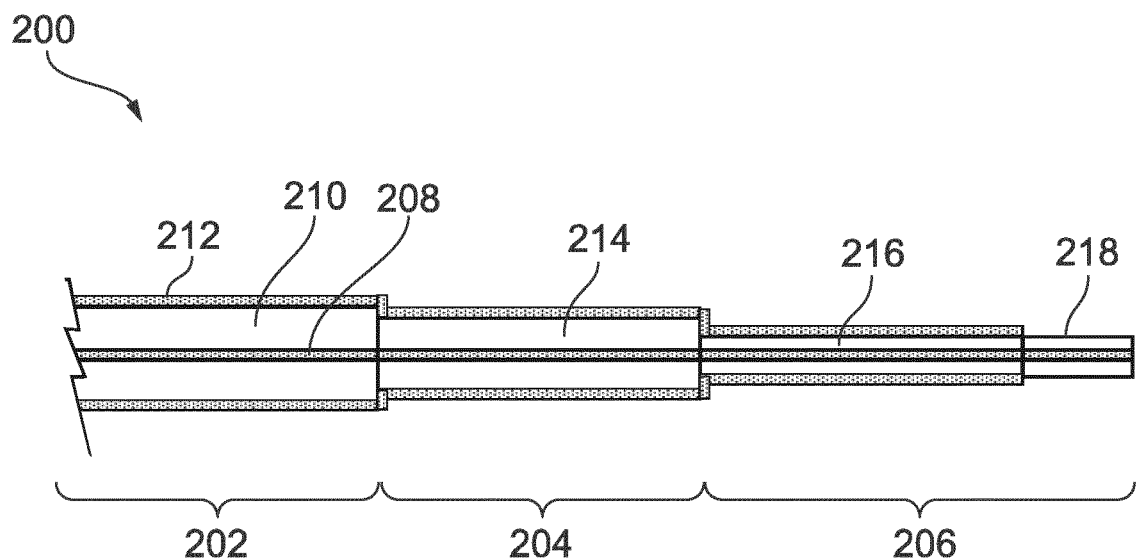
FIG. 3 is a longitudinal cross-sectional view through an ablation instrument that is an embodiment of the present invention.

FIG. 3 is a cross-sectional view of the distal end of an electrosurgical instrument 200 that is an embodiment of the invention. FIG. 3 shows a distal end portion of the instrument, which has three sections. A first section comprises a coaxial cable 202 which extends to a proximal end of the instrument, e.g. through the instrument channel of a surgical scoping device as discussed above. The proximal end of the coaxial cable 202 may be connected to an electrosurgical generator to receive and convey microwave energy, e.g. electromagnetic energy having a frequency of 5.8 GHz. A second section comprises an intermediate impedance transformer 204. A third section comprises a distal radiating portion 206. The intermediate impedance transformer 204 is arranged to match the impedance of the coaxial cable 202 to the impedance of the distal radiating portion 206.

The distal radiating portion 206 is dimensioned to be suitable for treating tissue in the pancreas. In particular its dimensions are similar to known probes that are used to penetrate into the pancreas through the wall of the duodenum, e.g. using an EUS device. A maximum outer diameter of the distal radiating portion 206 may thus be equal to or less than 1 mm (e.g. equal to or less than a 19 gauge needle). The length of the distal radiating portion may be around 40 mm.

The coaxial cable 202 may be a conventional flexible coaxial microwave cable having an outer diameter selected to enable it to pass through the instrument channel of a surgical scoping device. In one example, the outer diameter of the coaxial cable 202 may be equal to or less than 2.2 mm. For example, a Sucoform® 86 cable may be used. The coaxial cable comprises an inner conductor 208 that is separated from an outer conductor 212 by a insulating dielectric material 210. A protective jacket (not shown) may be provided around the outer surface of the outer conductor 212. The length of the coaxial cable 202 may be 1.2 m or more. Only a distal portion thereof is shown in FIG. 3.

In this embodiment, the inner conductor 208 of the coaxial cable 202 extends beyond the distal end of the outer conductor 212 through both the intermediate impedance transformer 204 and the distal radiating portion 206. All three sections of the distal end assembly therefore share a common inner conductor. In fact, in one example, the intermediate impedance transformer 204 and the distal radiating portion 206 may be formed by stripping the outer conductor from distal sections of the coaxial cable, selectively removing part of the dielectric material 210 to achieve a desired dielectric outer diameter for each portion, and then providing a new outer conductor over the reduced diameter portions. The intermediate impedance transformer 204 has a dielectric material 214 having a first reduced diameter, while the distal radiating portion 206 has a dielectric material 216 having a second reduced diameter. The first reduced diameter is less than the diameter of the dielectric material 210 in the coaxial cable 202. The second reduced diameter is less than the first reduced diameter. The relationship between the diameters is discussed in more detail below.

In this embodiment, the distal radiating portion 206 comprises a loaded monopolar antenna 218, which may be provided by removing the outer conductor from a distalmost length of the distal radiating portion 206. The loaded monopolar antenna 218 may have a length equal to an odd multiple of a quarter wavelength of the microwave energy conveyed by the coaxial cable 202.

As discussed above, it is desirable for the maximum outer diameter of the distal radiating portion 206 (which is the portion to be inserted into the pancreas) to be equal to or less than 1 mm. In one example, this is achieved by the following transverse dimensions for the relevant components:

TABLE 1

Dimensions for distal radiating portion 206

| Component | Outer diameter (mm) | Material |
|---|---|---|
| Inner conductor | 0.53 ($d_1$) | Cu/Ag plated steel |
| Dielectric | 0.85 ($d_2$) | PTFE |
| Outer conductor | 1.00 | Cu |

The thickness of the outer conductor in this example would be 0.075 mm. The relative permittivity $\varepsilon_r$ of the dielectric material used in this example is 1.85, which provides an impedance $Z_{out}$ for the distal radiating portion as follows:

$$Z_{out} = \frac{138}{\sqrt{\varepsilon_r}} \log_{10}\left(\frac{d_2}{d_1}\right) = 20.8 \Omega$$

Accordingly, given that the impedance $Z_{in}$ of the coaxial cable 202 is 50Ω, the impedance $Z_t$ of the intermediate impedance transformer 204 is calculated as $$Z_t = \sqrt{Z_{in} Z_{out}} = 32.251$$

Since in this example the same inner conductor and same dielectric material are used in the intermediate impedance transformer 204, the outer diameter $d_3$ of the dielectric material 214 can be calculated to satisfy the relation:

$$\frac{138}{\sqrt{\varepsilon_r}} \log_{10}\left(\frac{d_3}{d_1}\right) = 32.25 \Omega$$

Solving this gives $d_3$ as 1.1 mm. Following this, the transverse dimensions for the relevant components in the intermediate impedance transformer 204 may be as follows:

TABLE 2

Dimensions for intermediate impedance transformer 204

| Component | Outer diameter (mm) | Material |
|---|---|---|
| Inner conductor | 0.53 ($d_1$) | Cu/Ag plated steel |
| Dielectric | 1.1 ($d_3$) | PTFE |
| Outer conductor | 1.5 | Cu |

The length of the intermediate impedance transformer 204 is preferably an odd multiple quarter wavelength of the microwave energy conveyed therein. Where $\varepsilon_r$ is 1.85 mm, a quarter wavelength at 5.8 GHz is 9.5 mm.

If the same dielectric material is used for the whole length of the instrument, the length of the loaded monopolar antenna 218 may also be 9.5 mm. However, the same dielectric material need not be used everywhere. For example, a different dielectric material may be used for loaded monopolar antenna 218. For example, the length of the loaded monopolar antenna 218 may be reduced by using a dielectric material having a higher relative permittivity. In one example, a rigid dielectric material such as ceramic or polyether ether ketone (PEEK) could be used. In other example, the distal radiating portion 206 may comprise an unloaded antenna, e.g. a comprising a portion of exposed inner conductor. An example of this kind of structure is discussed with reference to FIG. 5 below.

The instrument 200 discussed above provides a means of introducing microwave energy into a pancreas that can facilitate more accurate and effective treatment than the radiofrequency-based techniques that have been used heretofore. In particular, the transport mechanism by which energy is delivered into device from a microwave antenna is primarily radiation. The target area is thus rapidly treated, and the risk of energy leakage or concentration in unwanted area is reduced. This may be in contrast to RF-based techniques in which the transport mechanism is primarily by conduction, and where the use of an externally positioned return pad can make the location of current paths difficult to control.

Although the instrument disclosed herein may be particularly suitable for use with microwave energy, the instrument may also provide a bipolar structure for delivering radiofrequency (RF) energy. In one example, the same structure that forms an antenna for radiating microwave energy provides an active electrode and a return electrode suitable for delivering RF energy therebetween. The active electrode may be the inner conductor. The return electrode may be a distal portion of the outer conductor. This arrangement provides a localised return path for the RF current, and hence may be preferable to the prior art instruments that require a separate external return pad. In other examples, the instrument may comprise a separate structure for delivering RF energy.

As discussed above, the instrument may be connectable to a generator that can deliver both RF and microwave energy separately or simultaneously along a coaxial transmission line. Accordingly, the instrument may be selectively operable in a plurality of treatment modes, e.g. comprising any one, two, three or more of: (i) microwave only, (ii) RF only, (iii) RF followed by microwave, (iv) microwave followed by RF, (v) RF and microwave simultaneously. The instrument is thus capable of performing treatment under more sophisticated energy application regimes that conventional RF ablation devices.

Figure 4:
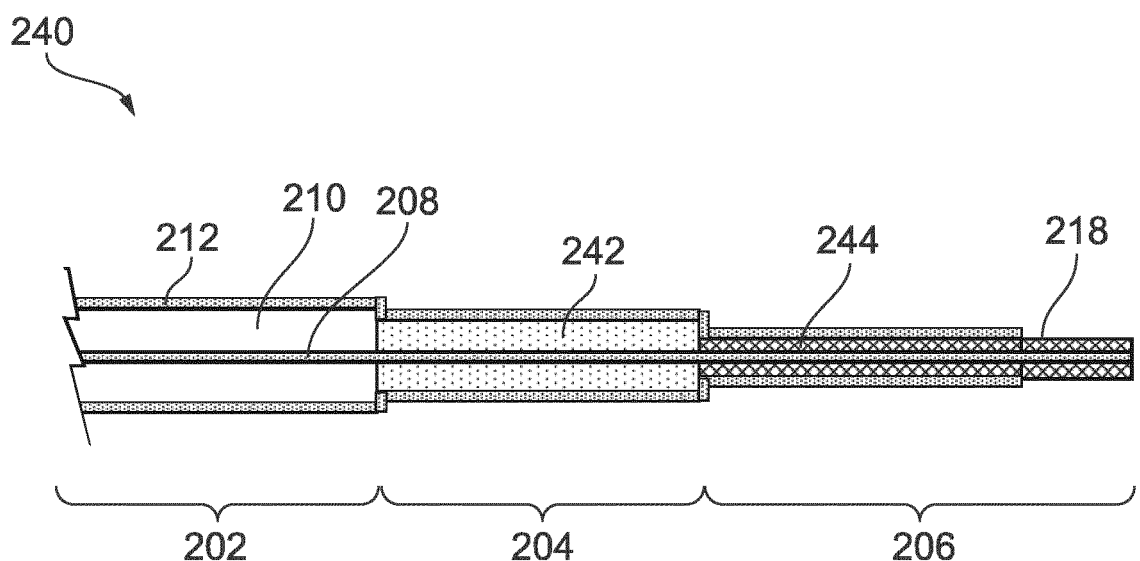
FIG. 4 is a longitudinal cross-sectional view through an ablation instrument that is another embodiment of the present invention.

FIG. 4 is a cross-sectional view of the distal end of an electrosurgical instrument 240 that is another embodiment of the invention. Features in common with the embodiment shown in FIG. 3 are given the same reference numbers and are not discussed again. Similar to FIG. 3, the instrument 240 utilises a common inner conductor from the coaxial cable 202 through the intermediate impedance transformer 204 and distal radiating portion 206. However, in this embodiment, the dielectric material of the coaxial cable 202 may be completely removed and replaced with alternative materials in the intermediate impedance transformer 204 and distal radiating portion 206.

It may be desirable for the distal parts of the instrument to be rigid in order to assist in pushing the instrument insider tumours to be treated. Accordingly, the intermediate impedance transformer 204 and distal radiating portion 206 may each be provided with a rigid dielectric material 242, 244. The rigid dielectric materials 242, 244 in this sections may be the same or different. For example, the intermediate impedance transformer 204 may have a dielectric material 242 formed form PEEK, whereas the distal radiating portion 206 may have a dielectric material 244 formed from ceramic, or vice versa. As explained above, an advantage of these materials is that they have a higher relative permittivity than the dielectric material 210 of the coaxial cable 202, which enables the distal portion to be compact. The rigid dielectric materials 242, 244 may be moulded around or otherwise mounted on the inner conductor 208 after the dielectric material 210 is stripped therefrom. As discussed above, a new outer conductor is applied over the intermediate impedance transformer 204 and relevant parts of the distal radiating portion 206 after the rigid dielectric materials 242, 244 are in place.

In a particular example having the structure shown in FIG. 4, the intermediate dielectric material 242 and distal dielectric material are both PEEK. The distal radiating portion 206 has a total length of 3 cm. The outer metallisation 244 extends over 2 cm of the total length, to leave a distalmost 1 cm portion of exposed PEEK (with the inner conductor running within). The outer metallisation 244 has an inner diameter of 0.8 mm and an outer diameter of 1.0 mm.

Figure 5:
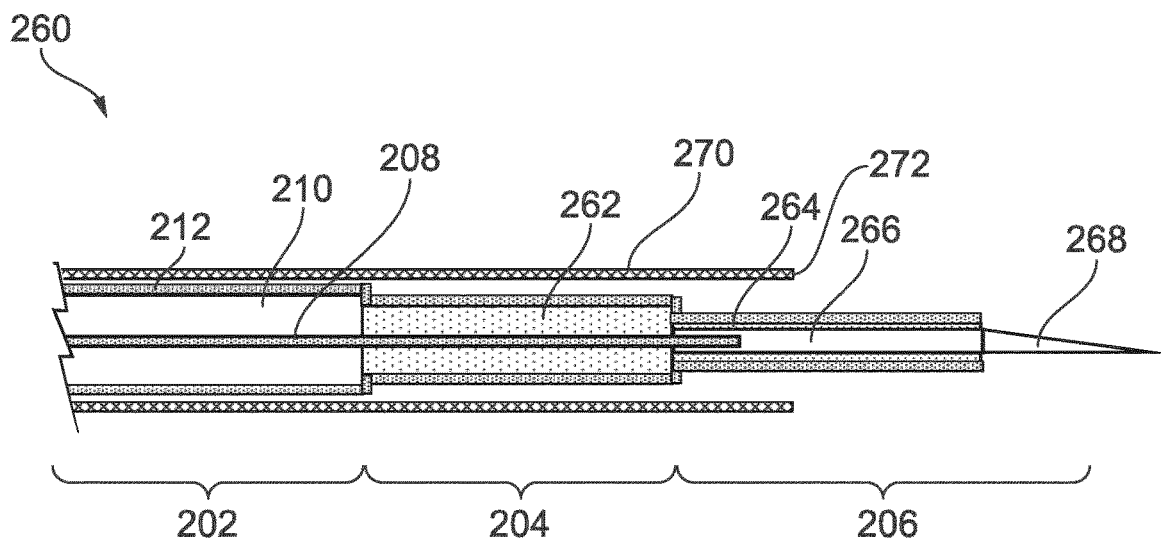
FIG. 5 is a longitudinal cross-sectional view through an ablation instrument that is another embodiment of the present invention.

FIG. 5 is a cross-sectional view of the distal end of an electrosurgical instrument 260 that is another embodiment of the invention. Features in common with the embodiment shown in FIG. 3 are given the same reference numbers and are not discussed again. In this example, the inner conductor 208 from the coaxial cable 202 extends through the intermediate impedance transformer 204 and terminates at a proximal end of the distal radiating portion 206. A rigid conductive finger 266 is mounted on an electrically connected to a distal end of the inner conductor 208. In this example, the rigid conductive finger 266 formed the inner conductor of the distal radiating portion 206 and protrudes therefrom as an unloaded monopole antenna 268. The protruding portion is sharpened, e.g. to resemble a needle, to facilitate insertion into tissue. The rigid conductive finger 266 may be made from stainless steel or the like.

In this example, the dielectric materials 262, 264 used in the intermediate impedance transformer 204 and the distal radiating portion 206 are different from the dielectric material 210 of the coaxial cable 202. As discussed above with reference to FIG. 4, these material may be chosen to impart desired physical properties (e.g. rigidity) or to control the length of the respective portion of the instrument. In the example shown, the outer diameter of the rigid conductive finger 266 may be greater than the outer diameter of the inner conductor 208, which will have an effect on the impedance of the distal portion.

The electrosurgical instrument 260 further comprises a retractable sheath 270 mounted over the coaxial cable 202. The sheath 270 is for controlling the depth of insertion and for protecting the lining of the instrument channel against damage due to the sharp tip of the antenna. The sheath 270 may extend over a distal portion of the instrument. It may have a calibrated scale (e.g. 1 mm to 30 mm), so that as the sheath is drawn back, the antenna is exposed. A distal end 272 of the sheath may be located against the wall of the duodenum whilst the antenna is inserted through the wall into the pancreas. The sheath end may thus act as a stop or reference point. The sheath may have an outer diameter sized to fit within the instrument channel. For example, it may be 2.4 mm or 2.7 mm. Although only illustrated in FIG. 5, it is to be understood that the sheath 270 may be used with any of the embodiments disclosed herein.

Figure 6:
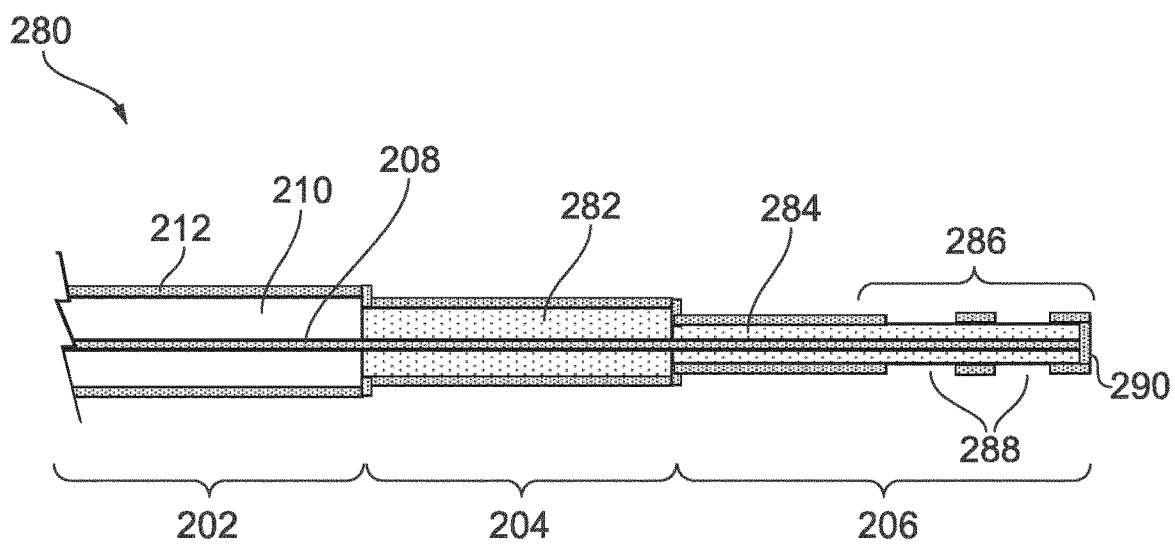
FIG. 6 is a longitudinal cross-sectional view through an ablation instrument that is another embodiment of the present invention.

FIG. 6 is a cross-sectional view of the distal end of an electrosurgical instrument 280 that is another embodiment of the invention. Features in common with the embodiment shown in FIG. 3 are given the same reference numbers and are not discussed again. In this example, the distal radiating portion 206 comprises a slotted antenna structure 286. Similar to FIG. 3, the instrument 280 utilises a common inner conductor from the coaxial cable 202 through the intermediate impedance transformer 204 and distal radiating portion 206. In this embodiment, the dielectric material of the coaxial cable 202 may be completely removed and replaced with alternative materials in the intermediate impedance transformer 204 and distal radiating portion 206. The intermediate impedance transformer 204 has a intermediate dielectric material 282 and the distal radiating portion 206 has a distal dielectric material 284. The intermediate dielectric material 282 and the distal dielectric material 284 may be the same or different. They may both differ from the dielectric material 210 of the coaxial cable.

To provide a compact slotted antenna, is may be desirable for the distal dielectric material 284 provide a high load to the structure, e.g. by having a dielectric constant equal to or greater than 20, preferably equal to or greater than 40. The slotted antenna 286 is formed by creating one or more windows or slots 288 in an outer conductive layer on the distal radiating portion 206. Where a plurality of slots are formed, there are separated along the length of the distal radiating portion 206 by half a wavelength of the microwave energy conveyed by the distal radiating portion 206. In order to create an elongated, i.e. forward directed, ablation field, a distal end of the inner conductor 208 may be electrically connected to the outer conductive layer on the distal radiating portion 206, e.g. via a conductive end cap 290. The distalmost slot on the distal radiating portion 206 is preferably spaced from the distal end (e.g. the end cap 290) by a quarter wavelength of the microwave energy conveyed by the distal radiating portion 206. In one example, the dielectric material 284 may have a relative permittivity of 49, whereby the quarter wavelength for microwave energy having a frequency of 5.8 GHz is 1.85 mm. In this example, the slots are spaced at 3.7 mm intervals along the length of the distal radiating portion 206.

In use, the instrument according to any of the examples set out above may be inserting through the instrument channel of an surgical scoping device to reach a treatment site, e.g. through the wall of the duodenum into the pancreas. The distal radiating portion 206 may penetrate tissue so that microwave energy delivered by the coaxial cable 202 is radiating into the tissue to ablate it.

In some procedures, an aspiration needle may be inserted to the treatment site before the instrument, e.g. to remove fluid from a cyst or the like.

The instrument of the invention may find particular use as an alternative to known RF ablation techniques, especially because the size of the instrument is of the same order as known RF probes, and can therefore be introduced using the same equipment.

The invention claimed is:

1. An electrosurgical instrument comprising:
a proximal portion comprising a coaxial transmission line for conveying microwave electromagnetic (EM) energy; wherein the coaxial transmission line comprises an inner conductor separated from a proximal outer conductor by a first dielectric material;
a distal radiating portion; and
an intermediate impedance transformer arranged to match an impedance of the coaxial transmission line to an impedance of the distal radiating portion,
wherein the inner conductor extends beyond a distal end of the proximal outer conductor through the intermediate impedance transformer and through the distal radiating portion to form a conductive portion of a microwave antenna for emitting the microwave EM energy conveyed by the coaxial transmission line,
wherein the microwave antenna comprises a distal dielectric material mounted over the conductive portion of the microwave antenna,
wherein the distal radiating portion defines an outer surface of the electrosurgical instrument and has a maximum outer diameter less than an outer diameter of the coaxial transmission line,
wherein the distal dielectric material has a maximum outer diameter less than an outer diameter of the first dielectric material, and
wherein the intermediate impedance transformer has a second dielectric material having a reduced diameter, the reduced diameter being less than the outer diameter of the first dielectric material and greater than the maximum outer diameter of the distal dielectric material.

2. The electrosurgical instrument according to claim 1, wherein the intermediate impedance transformer is a quarter wavelength coaxial transmission line.

3. The electrosurgical instrument according to claim 2, wherein, in the quarter wavelength coaxial transmission line, the inner conductor is separated from an intermediate outer conductor by the second dielectric material.

4. The electrosurgical instrument according to claim 3, wherein the second dielectric material is a reduced diameter portion of the first dielectric material that extends beyond the distal end of the proximal outer conductor.

5. The electrosurgical instrument according to claim 3, wherein the second dielectric material has a higher relative permittivity than the first dielectric material.

6. The electrosurgical instrument according to claim 1, wherein the microwave antenna is a loaded monopole antenna.

7. The electrosurgical instrument according to claim 1, wherein the distal dielectric material is a reduced diameter portion of the first dielectric material that extends beyond the distal end of the proximal outer conductor.

8. The electrosurgical instrument according to claim 1, wherein the distal dielectric material is a rigid material having a higher relative permittivity than the first dielectric material.

9. The electrosurgical instrument according to claim 1, wherein a distal end of the microwave antenna is sharpened to facilitate insertion into tissue.

10. The electrosurgical instrument according to claim 1, wherein the microwave antenna is a slotted antenna.

11. The electrosurgical instrument according to claim 10, wherein the distal radiating portion comprises a distal coaxial transmission line having a distal inner conductor separated from a distal outer conductor by the distal dielectric material, and wherein the slotted antenna is formed by removed portions of the distal outer conductor.

12. The electrosurgical instrument according to claim 11, wherein the distal inner conductor is electrically connected to the distal outer conductor at a distal tip of the microwave antenna.

13. The electrosurgical instrument according to claim 1, wherein the distal radiating portion comprises a bipolar structure for delivering radiofrequency (RF) energy.

14. The electrosurgical instrument according to claim 1, further comprising a bipolar structure formed by the microwave antenna.

15. The electrosurgical apparatus comprising:
a surgical scoping device having an instrument cord configured to be insertable into a patient's body, wherein the instrument cord has an instrument channel formed therethrough; and
an electrosurgical instrument according to claim 1 dimensioned to be insertable through the instrument channel.

16. The electrosurgical apparatus according to claim 15, wherein the surgical scoping device is an endoscopic ultrasound device.

17. The electrosurgical apparatus according to claim 15 further comprising an electrosurgical generator connected to supply radiofrequency (RF) energy and microwave energy to the coaxial transmission line separately or simultaneously, wherein the instrument is selectively operable in a plurality of treatment modes, the plurality of treatment modes comprising any of: (i) microwave only, (ii) RF only, (iii) RF followed by microwave, (iv) microwave followed by RF, (v) RF and microwave simultaneously.

* * * * *